Figure 1:
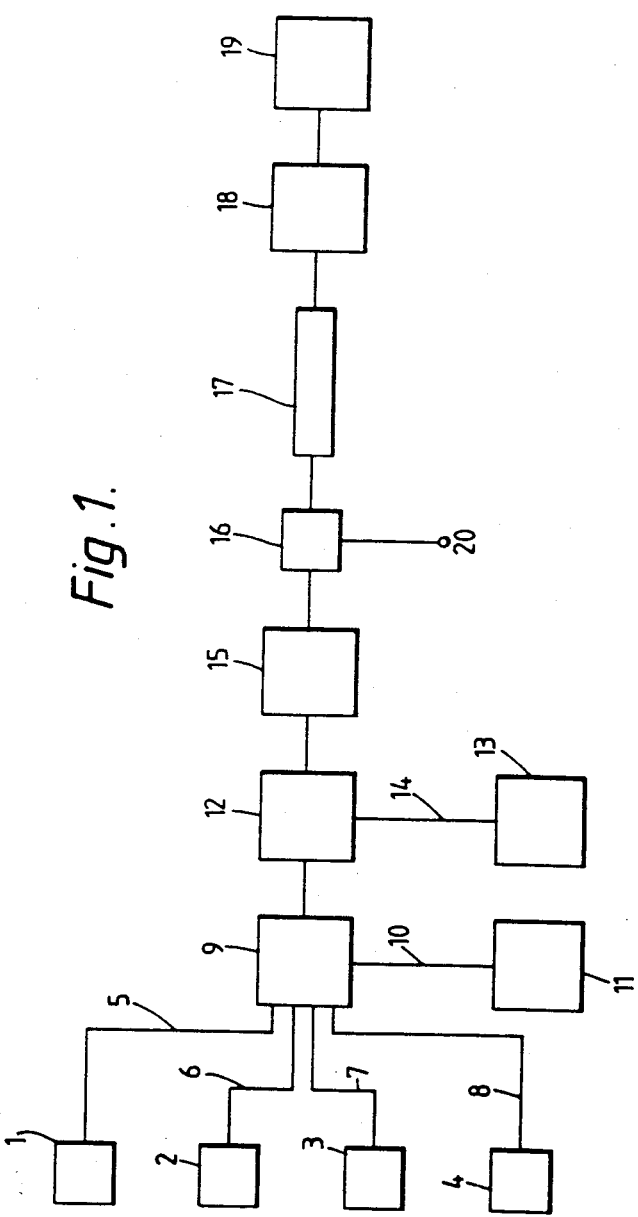

United States Patent [19]

James

[11] Patent Number: 4,902,414
[45] Date of Patent: Feb. 20, 1990

[54] LIQUID CHROMATOGRAPH APPARATUS

[75] Inventor: Phillip A. James, Mepal, England

[73] Assignee: U.S. Philips Corporation, New York, N.Y.

[21] Appl. No.: 339,936

[22] Filed: Apr. 18, 1989

Related U.S. Application Data

[63] Continuation of Ser. No. 106,083, Oct. 7, 1987, abandoned.

[30] Foreign Application Priority Data

Oct. 10, 1986 [GB] United Kingdom ............... 8624325

[51] Int. Cl.⁴ ............................................. B01D 15/08
[52] U.S. Cl. ............................ 210/198.2; 210/416.1; 210/501.1; 417/313
[58] Field of Search .............. 417/313, 539, 568; 210/101, 198.2, 416.1, 510.1; 422/70

[56] References Cited

U.S. PATENT DOCUMENTS

| | | | |
|---|---|---|---|
| 2,297,817 | 10/1942 | Truxell | 210/510.1 |
| 2,400,091 | 5/1946 | Alftan | 210/510.1 |
| 2,485,439 | 10/1949 | Erickson | 417/543 |
| 2,819,209 | 1/1958 | Pall | 210/510.1 |
| 2,842,267 | 7/1958 | Shire | 210/510.1 |
| 3,810,716 | 5/1974 | Abrahams | 417/313 |
| 4,045,343 | 8/1977 | Achener | 210/198.2 |
| 4,116,046 | 9/1978 | Stein | 210/198.2 |
| 4,116,837 | 9/1978 | Biermacher | 210/198.2 |
| 4,456,440 | 6/1984 | Korner | 417/540 |
| 4,457,846 | 7/1984 | Munk | 210/198.2 |
| 4,595,496 | 6/1986 | Carson | 210/198.2 |

Primary Examiner—Ernest G. Therkorn
Attorney, Agent, or Firm—Paul R. Miller

[57] ABSTRACT

A liquid chromatograph apparatus comprises a plurality of solvent sources (140,105) feeding a pump (102) via a proportioning valve arrangement (100). The proportioning valve arrangement (100) has a plurality of inlets (108,109) and a single outlet (110) which is coupled to the inlet coupling (112) of the pump (102). The inlet coupling (112) is mounted directly on the pump head (103) and incorporates a filter (118). The pump outlet (137) is fed via a tube (138) to a chromatographic separating column. The solvent sources (104,105) are coupled to the proportioning valve inlets (108,109) via tubes (106,107) without the provision of separate filters. This gives more equal average flow rates and enables more accurate proportioning of the solvent mixture to be obtained.

4 Claims, 3 Drawing Sheets

LIQUID CHROMATOGRAPH APPARATUS

This is a continuation of Ser. No. 106,083, filed 10/7/87, now abandoned.

The invention relates to liquid chromatograph apparatus comprising a plurality of solvent sources, a solvent proportioning valve arrangement having a separate inlet for each solvent and a single outlet, means for coupling the outlet of the proportioning valve arrangement to the inlet of a pump, means for coupling the outlet of the pump to the inlet of a chromatographic separating column, and means for detecting the constitutents eluting from the column.

In some applications of high performance liquid chromatography (HPLC) it is necessary to form the mobile phase from a mixture of two or more solvents. The mixture may remain constant with time or when using the technique known as gradient elution may be continously or stepwise varied with time. In both cases it is desirable to have as high an accuracy as possible in the proportions of the solvents in the mobile phase. The desired composition may be achieved by means of a proportioning valve arrangement which comprises a plurality of solenoid valves or similar devices which connect different solvent sources to the inlet of the pump sequentially during the suction stroke of the pump. The proportion of the duration of the suction period for which any one solvent is connected to the pump inlet determines the proportion of that solvent in the mobile phase. As disclosed in our co-pending British application No. 8622326, corresponding to U.S. application Ser. No. 94,579, filed Sept. 9, 1987 now abandoned, and assigned to the same assignee as the present application, the proportioning may take place over more than one pump or piston cycle. Further, as disclosed in our co-pending British application No. 8622328, corresponding to U.S. application Ser. No. 94,625, filed Sept. 9, 1987 now abandoned, and assigned to the same assignee as the present application, the proportioning valve arrangement may be constructed to minimise liquid flow surges caused by quickly operating valves.

In practical embodiments of such solvent proportioning systems a filter is inserted in each of the solvent supply lines. Customarily these filters are located within each individual solvent container on the end of the tube which leads from the solvent container to the proportioning valve arrangement.

It is an object of the invention to enable the provision of liquid chromatograph apparatus in which two or more solvents can be accurately proportioned into a mixture forming a desired mobile phase, the proportioning taking place at low pressure prior to the pumping system.

The invention provides liquid chromatograph apparatus as set forth in the opening paragraph characterised in that the means for coupling the outlet of the proportioning valve arrangement to the inlet of the pump comprises a filter.

A number of advantages are obtained by providing a single filter at the inlet of the pump instead of individual filters at each solvent source. If separate filters are used it is likely that there will be a variation in their impedance to liquid flow and consequently inaccuracies in the solvent proportions will then occur since the average flow rates of the individual solvents into the pump inlet will vary when switching from one solvent source to another. The variation in impedance to the flow of the solvents will be much reduced without the presence of individual filters since the impedance of the solvent supply tubes is small. The pressure differential in the solvent supply tubes is reduced as the high impedance filter is between the proportioning valve arrangement and the inlet to the pump and this reduces the likelihood of sucking air into the system at the tube joints. A single filter after the proportioning valve arrangement is less expensive than a plurality of separate filters which are necessary prior to the valve arrangement if no subsequent flter is used.

The filter may be mounted on the inlet means of the pump. Thus the major flow resistance on the inlet side of the pump is located adjacent the inlet and hence the pressure differential in the rest of the system is reduced.

Figure 2:
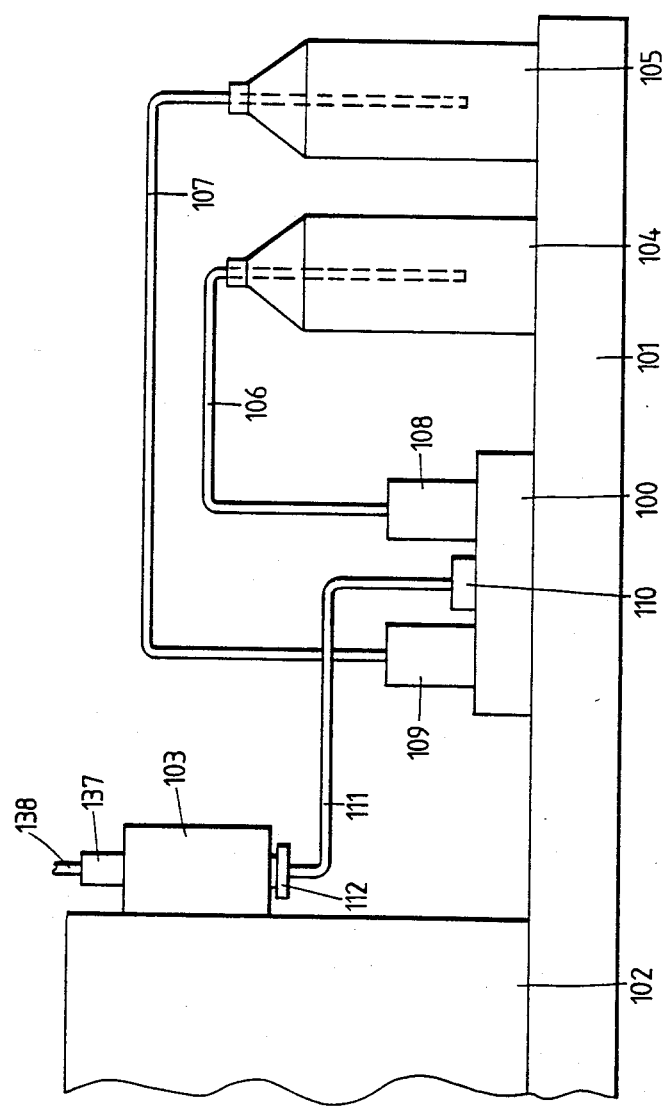
Figure 3:
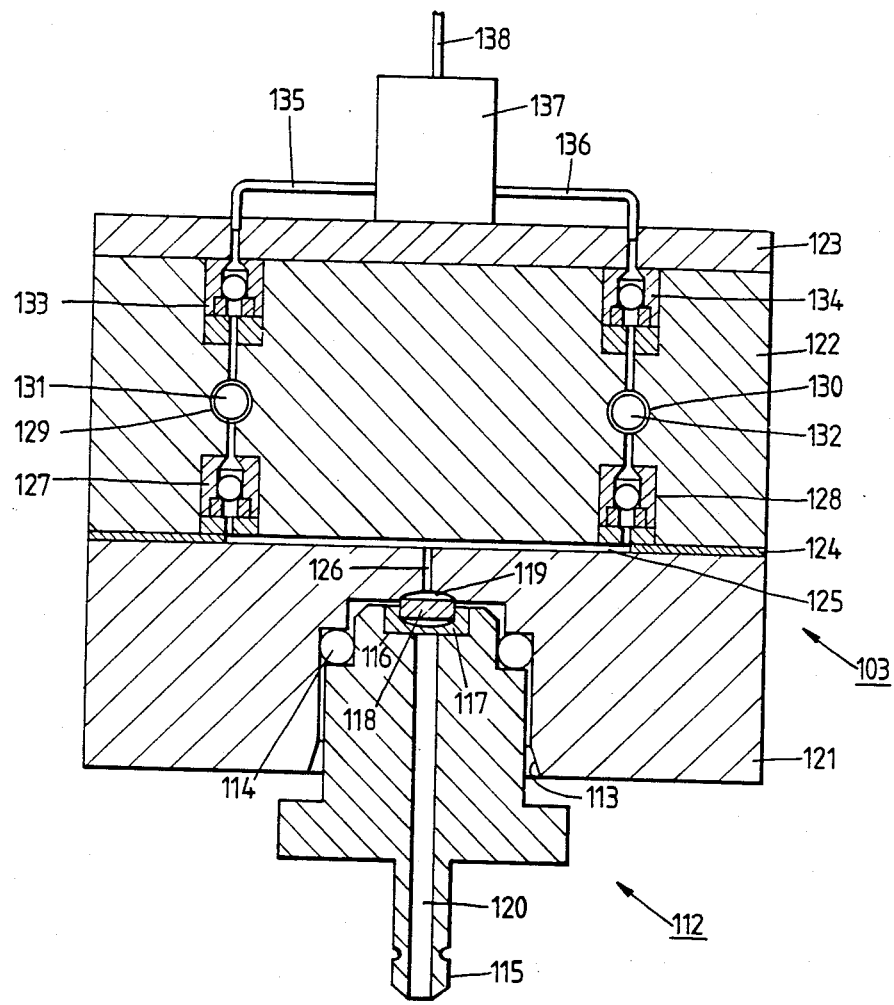

An embodiment of the invention will now be described, by way of example, with reference to the accompanying drawings, in which:

FIG. 1 shows in block schematic form liquid chromatograph apparatus according to the invention, FIG. 2 shows diagrammatically the solvent supply arrangement connected to the inlet of the pump, and FIG. 3 shows in cross-section the mounting of a filter on the pump head assembly.

The liquid chromatograph apparatus shown in FIG. 1 comprises four solvent reservoirs 1 to 4, which are fed via individual tubes 5 to 8 to the inlets of a proportioning valve arrangement 9. The proportioning valve arrangement is electrically operated and is controlled over line 10 from a solvent proportioning control arrangement 11. The outlet of the proportioning valve arrangement 9 is fed to the inlet of a pump 12. The pump 12 is controlled by means of a pump control circuit 13 over a line 14. The outlet from the pump 12 is fed to the inlet of a solvent mixer 15 whose outlet feeds a sample injection means 16. The outlet of the sample injection means 16 is fed to the input of a separating column 17 whose outlet is fed to a detector 18. The output of the detector 18 is fed to a signal processing and display arrangement 19. A second port of the sample injection means 16 is fed with a sample via a sample inlet 20.

In operation a selected solvent is fed to the pump 12 via the proportioning valve arrangement 9. The proportioning valve arrangement 9 selects each of the solvent sources 1 to 4 in proportion to the desired composition of the solvent to be fed to the pump, that is the solvent proportioning control arrangement operates the appropriate valves at the appropriate times to feed either a selected one of the solvents 1 to 4 or to feed in quick succession two or more solvents to the pump inlet during the suction stroke of the pump to provide a mixture of two or more solvents to be fed to the column. The pump control circuit 13 controls the speed of the pump to obtain the desired flow rate of the solvent. The solvent mixer 15 ensures that the various components of the solvent to be fed to the column are thoroughly mixed together and comprises a tapering enclosed chamber having an inlet located adjacent its larger end and an outlet located adjacent its smaller end. The solvent mixer 15 is an optional component of the system and may not be required under all operating conditions. Its use will depend on the system construction and it may be by-passed under certain conditions and in some systems may be omitted. Further, it could be replaced by other forms of solvent mixer either static or dynamic. The proportioning valve arrangement 9 may be provided, adjacent to the inlet to each valve, with a chamber having a solvent inlet and a solvent outlet, the chamber being partially occupied by air or a gas or mixture of gases. This chamber is located close to the inlet port of each valve and relatively distant from the respective solvent containing vessel 1 to 4. For details of this proportioning valve arrangement reference should be made to our co-pending British application No. 8622328, corresponding to U.S. application Ser. No. 94,625, filed Sept. 9, 1987 now abandoned, and assigned to the same assignee as the present application.

Hitherto solvent mixing arrangements using a plurality of solvent sources and a proportioning valve arrangement prior to the inlet of the pump have included separate filters in each solvent supply path. Traditionally the solvent sources have comprised enclosed containers or bottles having a tube leading from them to the corresponding inlet of the proportioning valve arrangement. A filter has been provided on the end of the tube within the solvent container to prevent solid particles entering the pump and hence the separating column. The provision of the separate filters in the sample containers produces a number of problems particularly where accurate proportioning of the solvents is required and proportioning is achieved by means of proportioning valve arrangement which sequentially connects the solvent sources to the pump inlet during the suction stroke of the pump. If there is a difference between the flow resistances of the various filters then the average flow rates of the solvents into the pump will not be equal and hence inaccuracies in proportioning will occur since the timing of the valve switching the proportioning valve arrangement assumes equal solvent flow rates. Since the filters provide a significant flow resistance a pressure differential exists between the inlet of the pump and the solvent sources. This leads to the risk of sucking air into the system if joints between the various tubes, valve inlets and outlet, and the pump inlet are not perfect. By locating the filter at the pump inlet, where the seal can be carefully constructed, the pressure differential in the rest of the solvent supply arrangement is reduced and hence the risk of sucking air into the system is correspondingly reduced. Further by locating the filter after the proportioning valve arrangement the number of filters required is reduced and the cost of the system can be correspondingly reduced.

As shown in FIG. 2 a proportioning valve arrangement 100 is mounted on a base 101 which also carries a pump 102 having a pump head 103. Two solvent sources in the form of containers 104 and 105 are connected via respective tubes 106 and 107 to inlets 108 and 109 of the proportioning valve arrangement 100. An outlet 110 of the proportioning valve arrangement 100 is connected via a tube 111 to an inlet coupling 112 on the pump head 103. The inlet coupling 112 connects the end of the tube 111 to the inlet of the pump head 103 and also serves as a housing locating a filter. The pump 102 may be as described in our co-pending British application No. 8523014, corresponding U.S. application Ser. No. 908,465, filed Sept. 17, 1986 now U.S. Pat. No. 4,752,385, and assigned to the same assignee as the present application.

FIG. 3 shows the pump head 103 and inlet coupling 112 in cross-section. The inlet coupling 112 is a close fit in a recess 113 of the pump head 103. An O-ring 114 provides an air and liquid tight seal between the recess 113 and the inlet coupling 112. The inlet coupling 112 is circular in cross-section and is provided with a projection 115 on which the tube 111 fits. A recess 116 in the inlet coupling 112 houses a PTFE block 117 which locates a disc filter 118 in close proximity to a part spherical depression 119 in the recess 113. A passageway 120 extends through the inlet coupling 112 to allow liquid to flow from the tube 111 to the filter 118.

The pump head 103 comprises three blocks 121, 122 and 123 which are clamped together. The blocks 121 and 122 sandwich a spacer 124 which includes a slot 125 to enable a passageway 126 in block 121 to communicate with inlet check valves 127 and 128 housed in block 122. The block 122 has two cylinders 129 and 130 machined in it; the cylinders containing pistons 131 and 132 and communicating with respective inlet check valves 127 and 128 and outlet check valves 133 and 134. The outlet check valves connect via tubes 135 and 136 to a combining block 137 which has an outlet 138 for connection to the chromatograph column.

The filter 118 comprises a sintered disc of, for example stainless steel or PTFE. The inlet coupling 112 is designed for easy removal from the pump head 103 to enable periodic replacement of the filter 118 as it becomes blocked with debris. The inlet coupling 112 could alternatively be connected to the pump head 103 by means of a screw thread or any other means which would allow disconnection to enable the filter 118 to be replaced.

When the inlet coupling 112 takes the form shown in FIG. 3 the filter 118 will not seat firmly against the depression 119 as the resilience of the O-ring 114 will spring the inlet coupling 112 away from the inner surface of the recess 113. Consequently solvent may be able to leak past the filter 118 into the gap between the inlet coupling 112 and the recess 113. However, the O-ring 114 will prevent liquid escaping. This construction is satisfactory in some circumstances but can lead to dead volumes of liquid which may carry over undesirably into different solvent compositions. To avoid this a screw coupling may be provided and the PTFE block 117 extended upwardly around the filter 118 so that when the screw thread is tightened the block 117 seals against the recess and prevents liquid from escaping round the edges of the filter 118.

While it is convenient to locate the filter 118 at the pump inlet it would be possible to mount it on the outlet of the proportioning valve arrangement and still obtain most of the advantages of the invention. The advantage of equal solvent flow rates would still be obtained as well as minimising the number of components required (and hence the cost of the apparatus). Further the pressure differential caused by the filter would only affect the connection between the outlet of the proportioning valve arrangement and the inlet of the pump.

Clearly alternative constructions could be used and the invention is not limited to the particular form of pump, filter, or proportioning valve arrangement described in the embodiment. The form of the filter may be chosen to suit a particular pump construction or proportioning valve arrangement.

I claim:

1. A liquid chromatograph apparatus comprising:
a plurality of solvent sources,
pump means for pumping solvent,
proportioning valve means for feeding solvent from said plurality of solvent sources to said pump means, said proportioning valve means having a separate inlet for each solvent from said plurality of solvent sources, said separate inlet for each solvent from said plurality of solvent sources providing a low impedance path by being free of filters, and said proportioning valve means having a single outlet, first means for coupling said single outlet of said proportioning valve means to an inlet of said pump means, said first means including a sintered filter disc, a chromatographic separating column, second means for coupling an outlet of said pump to an inlet of said chromatographic separating column, third means for providing a sample to said chromatographic separating column, and detecting means for detecting constituents eluding from chromatographic separating column.

2. A liquid chromatograph apparatus according to claim 1, wherein an inlet coupling is disposed at said inlet to said pump means, and wherein said sintered filter disc is provided in said inlet coupling.

3. A liquid chromatograph apparatus according to claim 3, wherein said inlet coupling includes a block of PTFE locating said filter at said sintered inlet disc of said pump means.

4. A liquid chromatograph apparatus according to claim 1 or claim 2, wherein said sintered filter disc includes one of sintered stainless steel or of PTFE.

* * * * *